(12) United States Patent
Behrend et al.

(10) Patent No.: US 8,774,892 B2
(45) Date of Patent: *Jul. 8, 2014

(54) ELECTRODE CONFIGURATION AND MEASURING DEVICE FOR MEASURING THE ELECTRICAL ACTIVITY IN ELECTRICALLY ACTIVE TISSUE

(75) Inventors: Detlef Behrend, Rostock-Warnemünde (DE); Klaus-Peter Schmitz, Rostock-Warnemünde (DE); Hans Wilhelm Pau, Rostock (DE); Katrin Sternberg, Rostock (DE); Wolfram Schmidt, Rostock (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 678 days.

This patent is subject to a terminal disclaimer.

(21) Appl. No.: 12/763,374

(22) Filed: Apr. 20, 2010

(65) Prior Publication Data

US 2010/0268054 A1 Oct. 21, 2010

Related U.S. Application Data

(63) Continuation-in-part of application No. 12/601,156, filed as application No. PCT/EP2008/056944 on Jun. 4, 2008.

(30) Foreign Application Priority Data

Jun. 5, 2007 (DE) .......................... 10 2007 026 645
May 6, 2009 (DE) .......................... 10 2009 020 156

(51) Int. Cl.
*A61B 5/0492* (2006.01)

(52) U.S. Cl.
USPC ............................ 600/379; 600/373; 600/546

(58) Field of Classification Search
USPC ......... 600/372, 373, 377, 379, 393, 546, 552, 600/559; 607/116, 137, 118; 606/51, 52
See application file for complete search history.

(56) References Cited

U.S. PATENT DOCUMENTS 1,714,220 A * 5/1929 Groff .............................. 606/51
3,313,293 A * 4/1967 Chesebrough et al. ........ 600/373

(Continued)

FOREIGN PATENT DOCUMENTS

| DE | 102008048984 | 9/2008 | |
| GB | 2320193 A | 6/1998 | ........... A61B 5/0492 |
| WO | WO 2010/038393 | 4/2010 | ........... A61B 5/0476 |

OTHER PUBLICATIONS

International Bureau of WIPO, International Search Report, PCT/EP2008/056944, dated Jan. 12, 2010.

(Continued)

*Primary Examiner* — Lee S Cohen
*Assistant Examiner* — Erin M Cardinal
(74) *Attorney, Agent, or Firm* — Sunstein Kann Murphy & Timbers LLP

(57) ABSTRACT

An electrode arrangement for sensing electrical activity in target tissue is described. A support electrode has an elongate electrode body with a base end and a penetrating end for insertion into the target tissue. A fixation electrode has an elongate electrode body with a base end and a penetrating end at an angle to the electrode body. The electrodes are joined together with their electrode bodies in parallel so that the penetrating end of the fixation electrode penetrates a fixed distance into the target tissue so that at least one of the electrodes senses electrical activity in the target tissue.

11 Claims, 8 Drawing Sheets

(56) References Cited

U.S. PATENT DOCUMENTS

| | | | | |
|---|---|---|---|---|
| 3,682,162 | A | * | 8/1972 | Colyer .................. 600/373 |
| 4,590,946 | A | | 5/1986 | Loeb .................... 600/375 |
| 4,671,274 | A | * | 6/1987 | Sorochenko ............ 606/51 |
| 5,269,780 | A | * | 12/1993 | Roos .................... 606/42 |
| 5,322,055 | A | * | 6/1994 | Davison et al. ......... 601/2 |
| 5,545,219 | A | * | 8/1996 | Kuzma .................. 623/10 |
| 6,010,516 | A | * | 1/2000 | Hulka ................... 606/148 |
| 6,030,384 | A | * | 2/2000 | Nezhat .................. 606/48 |
| 6,205,360 | B1 | | 3/2001 | Carter et al. ............ 607/57 |
| 6,208,882 | B1 | | 3/2001 | Lenarz et al. ........... 600/379 |
| 6,273,887 | B1 | * | 8/2001 | Yamauchi et al. ....... 606/48 |
| 6,478,794 | B1 | * | 11/2002 | Trapp et al. ............ 606/45 |
| 6,936,006 | B2 | * | 8/2005 | Sabra .................... 600/300 |
| 2002/0120263 | A1 | * | 8/2002 | Brown et al. ........... 606/41 |
| 2005/0216073 | A1 | | 9/2005 | Jolly et al. .............. 607/137 |
| 2005/0261602 | A1 | | 11/2005 | Mumford et al. ....... 600/546 |
| 2011/0282177 | A1 | * | 11/2011 | Behrend et al. ......... 600/386 |

OTHER PUBLICATIONS

European Patent Office, International Search Report and Written Opinion, PCT/US2011/032952, dated Jul. 13, 2011.

Clement, R.S., et al, "Characteristics of Stapedius Muscle Electromyograms Elicited by Cochlear Implant Stimulation in the Rat", *Proceedings of the 26th Annual International Conference of the IEEE EMBS*, San Francisco, CA, Sep. 1-5, 2004; XP-002495109.

\* cited by examiner

ELECTRODE CONFIGURATION AND MEASURING DEVICE FOR MEASURING THE ELECTRICAL ACTIVITY IN ELECTRICALLY ACTIVE TISSUE

This application is a continuation in part of co-pending U.S. patent application Ser. No. 12/601,156, filed Nov. 20, 2009, which in turn is a national phase entry of Patent Cooperation Treaty Application PCT/EP2008/056944, filed Jun. 4, 2008, which in turn claims priority from German Patent Application 10 2007 026 645.8, filed Jun. 5, 2007; and also claims priority from German Patent Application 10 2009 020 156, filed May 6, 2009; all of which are incorporated herein by reference.

FIELD OF THE INVENTION

The present invention relates to an electrode configuration and a measuring device for measuring the action current and/or the action potential of electrically active tissue, specifically a bipolar stapedius muscle electrode configuration for measuring the action potential generated upon a contraction of the stapedius muscle.

BACKGROUND ART

The human ear may be divided into the following areas: outer ear (auricle), middle ear, and inner ear. The middle ear comprises the eardrum and the auditory ossicles hammer, anvil, and stirrup. The eardrum is caused to oscillate via sound waves entering the outer ear. These oscillations may be transmitted via hammer, anvil, and stirrup to the oval window of the inner ear, by which sound oscillations may in turn be generated in the liquid of the cochlea. The hair cells projecting into the cochlea are bent by the movement of the liquid and thus trigger nerve pulses. A mechanical impedance conversion occurs in the middle ear, which allows an optimum transmission of the sound signal from the outer ear to the inner ear.

In addition, the tympanic muscle and the so-called stapedius muscle are located in the middle ear. The tympanic muscle is linked to the hammer, the stapedius muscle being connected via a tendon to the stirrup. In case of an excessively high sound pressure, which could damage the inner ear, both muscles contract reflexively, so that the mechanical coupling of the eardrum to the inner ear (and thus also the force transmission) is decreased. In this way, it is possible to protect the inner ear from excessively high sound pressures. The tensing of the stapedius muscle triggered as a result of high sound pressures is also referred to as the stapedius reflex. Medically relevant information about the functional capability of the ear may be obtained from the diagnosis of the stapedius reflex. Furthermore, the measurement of the stapedius reflex is useful for setting and/or calibrating so-called cochlear implants, because the sound energy perceived by a patient may be concluded from the measured stapedius reflex.

Using electrodes, which are brought into contact with the stapedius muscle and which relay action current and/or action potentials generated upon a contraction of the stapedius muscle to a measuring device, is known for measuring the stapedius reflex. A reliable, minimally-invasive contact of the stapedius muscle is difficult, because the stapedius muscle is situated inside a trough present in a bone and only the tendon of the stapedius muscle connected to the stirrup and its upper part are accessible from the interior of the middle ear.

Various stapedius muscle electrodes are known from U.S. Pat. No. 6,208,882. However, these only achieve inadequate contact of the stapedius muscle tissue (in particular upon muscle contraction) and are also very traumatizing.

DE 10 2007 026 645 A1 discloses a two-part bipolar electrode configuration where a first electrode is pushed onto the tendon of the stapedius muscle or onto the stapedius muscle itself, and a second electrode is pierced through the first electrode into the stapedius muscle. One disadvantage of the described solution is its rather complicated handling in the very limited space of a surgical operation area. In addition, the piercing depth of the second electrode is not controlled so that trauma can also occur with this approach.

It would be advantageous to have a simple cost effective electrode for measuring action currents and/or action potentials in electrically active tissues (such as the stapedius muscle tissue), which enables secure but reversible fixing of the electrode in the target tissue, but which traumatizes the tissue as little as possible.

SUMMARY OF THE INVENTION

Embodiments of the present invention are directed to an electrode arrangement for sensing electrical activity in target tissue. A support electrode has an elongate electrode body with a base end and a penetrating end for insertion into the target tissue. A fixation electrode has an elongate electrode body with a base end and a penetrating end at an angle to the electrode body. The electrodes are joined together with their electrode bodies in parallel so that the penetrating end of the fixation electrode penetrates a fixed distance into the target tissue so that at least one of the electrodes senses electrical activity in the target tissue.

The electrode body of the support electrode may include an inner cylindrical section surface, in which case, the electrode body of the fixation electrode may fit into the inner cylindrical section surface of the support electrode. There may be an electrode opening towards the penetrating end of the support electrode through which fits the penetrating end of the fixation electrode. And there may be an electrical insulation layer in the electrode opening for electrically isolating the support electrode from the fixation electrode. For example, the insulation layer may include a material from at least one of ceramic, sapphire, A2O3, TiO2, and glass, and/or have a thickness between 10 µm and 30 µm. The penetrating end of the fixation electrode may form a right angle to the electrode body.

There may be an electrical output connection to provide an electrical output signal representing the sensed electrical activity. The base end of the fixation electrode may be mechanically connected to the base end of the support electrode. A (moveable) fixation connector may surround the electrode bodies and mechanically connect the electrodes. The target tissue may include stapedius muscle tissue. The electrode arrangement may form either a monopolar or bipolar sensing arrangement. There may be an insulation layer covering at least a portion of at least one of the electrodes. For example, the insulation layer may include a material from at least one of silicone and polyurethane elastomer.

Embodiments of the present invention also relate to a method for determining the action current and/or the action potential of electrically active tissue in which an electrode configuration is brought into contact with electrically active target tissue and/or pierced into the tissue; for example, muscle tissue such as the stapedius muscle.

Embodiments of the invention also include an in vitro method where ex corporeal electrically active tissue is used for research and/or teaching purposes. Alternatively, embodiments of the invention can also be used in vivo for therapeutic purposes. In either in vitro or in vivo arrangements, the electrode configuration is guided in the open state to the electrically active target tissue and subsequently the tip of the support electrode is pierced into the tissue. When the desired piercing depth has been reached, a base joint in the electrode arrangement is closed. The tip of the fixation electrode is automatically also inserted into the electrically active tissue. In embodiments that measure the action potential of the stapedius muscle, the electrode configuration is guided along the tendon of the muscle up into the proximity of the muscle and then advanced until the tip of the support electrode has reached the required piercing depth in the muscle tissue. The base joint is then closed, so that the tip of the fixation electrode also pierces into the muscle tissue. The piercing point of the fixation electrode is in front of the piercing point of the support electrode, viewed from the operator. The muscle is accessible in the operating region, and the tendon can be used as a placement orientation. As a second variant, the piercing point of the fixation electrode may not be in the muscle, but rather outside on the tendon. The fixation electrode can nonetheless be used as a reference electrode for a bipolar potential derivation.

Embodiments of the present invention also include a kit which contains an electrode configuration as described herein together with written information, such as a data sheet or instructions and/or means for use, such as means for holding, guiding, and placing, such as adapters and/or surgical instruments. The kit can be used for in vitro experiments by scientists or for in vivo applications by appropriately qualified surgeons. The written information and the means for use are adapted accordingly.

DETAILED DESCRIPTION OF SPECIFIC EMBODIMENTS

Figure 1:
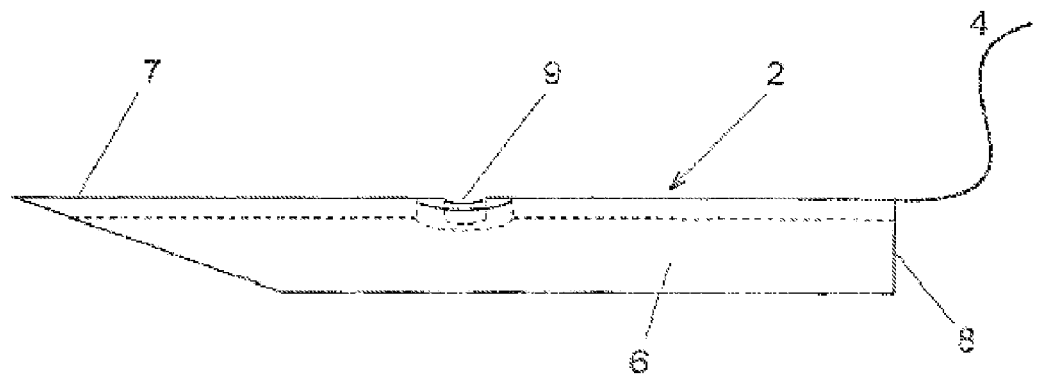
FIG. 1 shows the first electrode of a two-part electrode configuration according to the invention in a schematic, sectional illustration.
Figure 2:
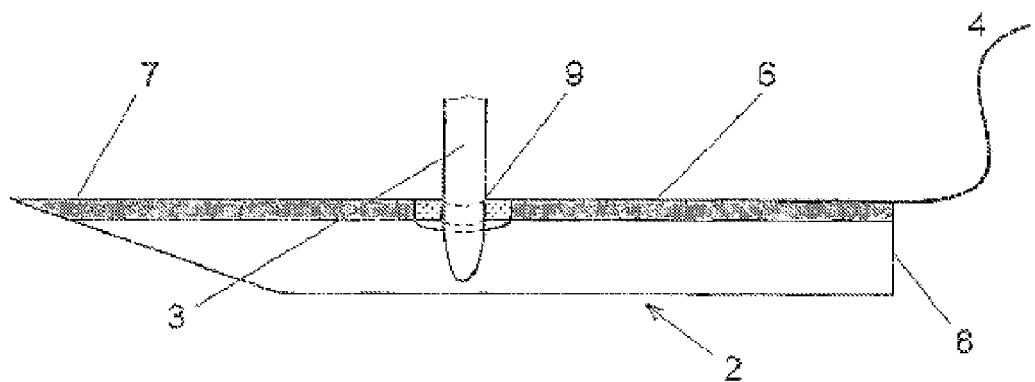
FIG. 2 shows an electrode configuration according to the invention in a schematic, sectional illustration, in which the second electrode is plugged into the first electrode for the fixation.
Figure 3:
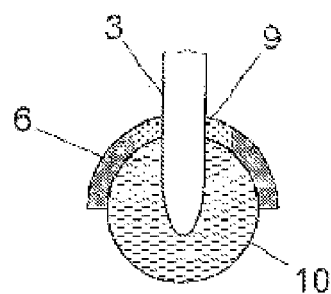
FIG. 3 shows the electrode configuration according to the invention from FIG. 2 in a schematic sectional illustration perpendicular to the longitudinal axis of the first electrode.
Figure 4:
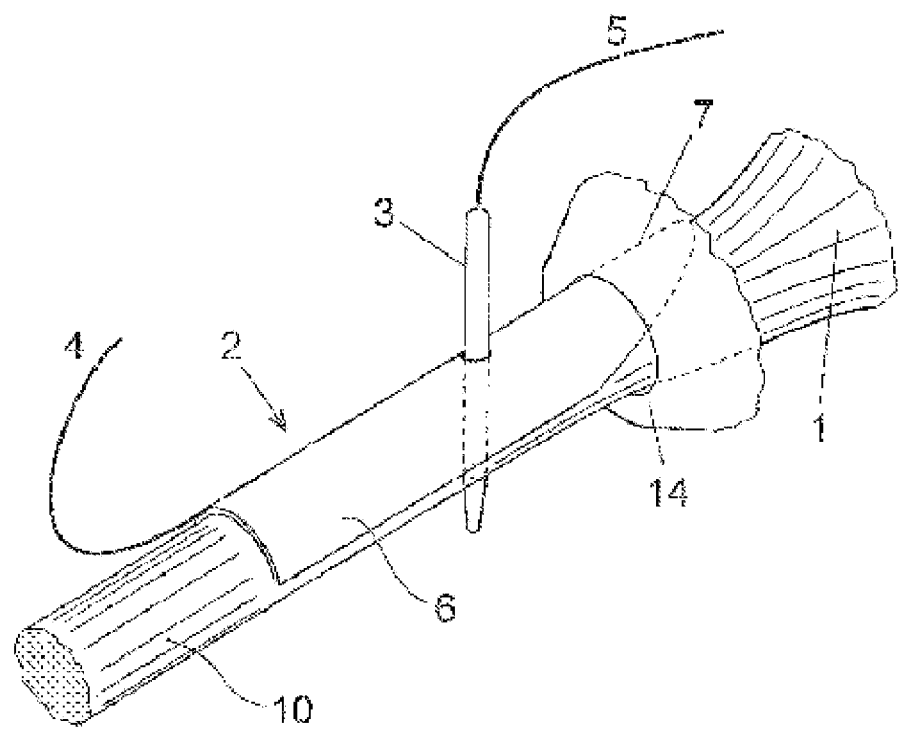
FIG. 4a shows the electrode configuration according to the invention, fastened on a stapedius muscle tendon, in a perspective illustration.
FIG. 4b shows the electrode configuration according to the invention, fastened on a stapedius muscle tendon, in a sectional illustration.
Figure 4:
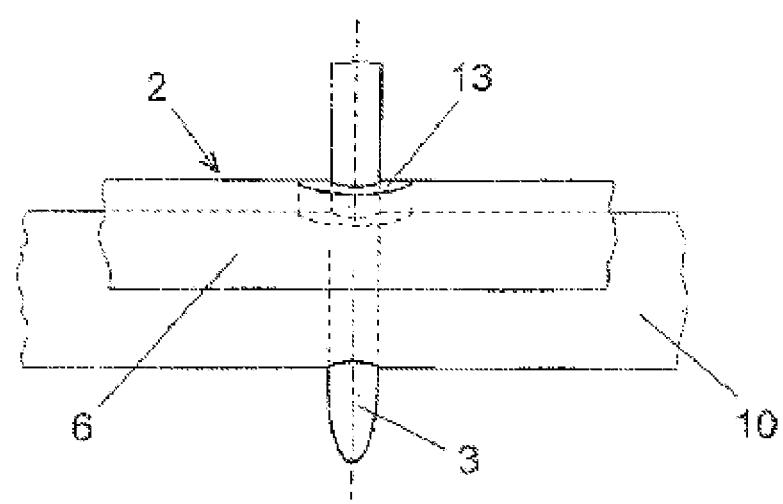
Figure 5:
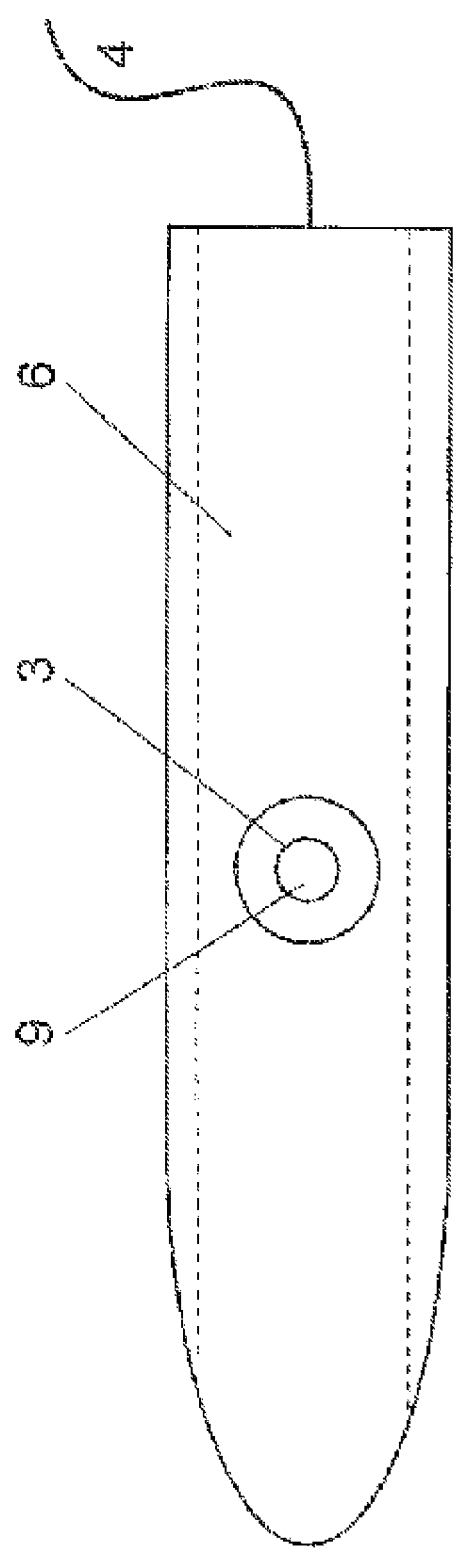
FIG. 5 shows the electrode configuration according to the invention from FIG. 2 in a top view.

FIG. 1 shows a (first) electrode 2 of the electorate configuration according to the invention in a schematic, sectional illustration. According to the invention, the first electrode 2 comprises an elongate main body 6, which, in an especially preferred embodiment variant, is implemented in the form of a half hollow cylinder (hollow cylinder open along its longitudinal axis having a center point angle of approximately 180°) made of a conductive material. Furthermore, it is provided that an electrical supply line 4 is connected to the main body 6 in the area of the second end 8. The electrical supply line 4 is preferably electrically insulated. In the area of the first end 7, the hollow-cylindrical main body 6 preferably has a bevel in the angle range from 30° to 60°. Because of its oblong shape, it is only possible to guide the main body 6 through tissue 1 along its longitudinal axis.

Figure 6:
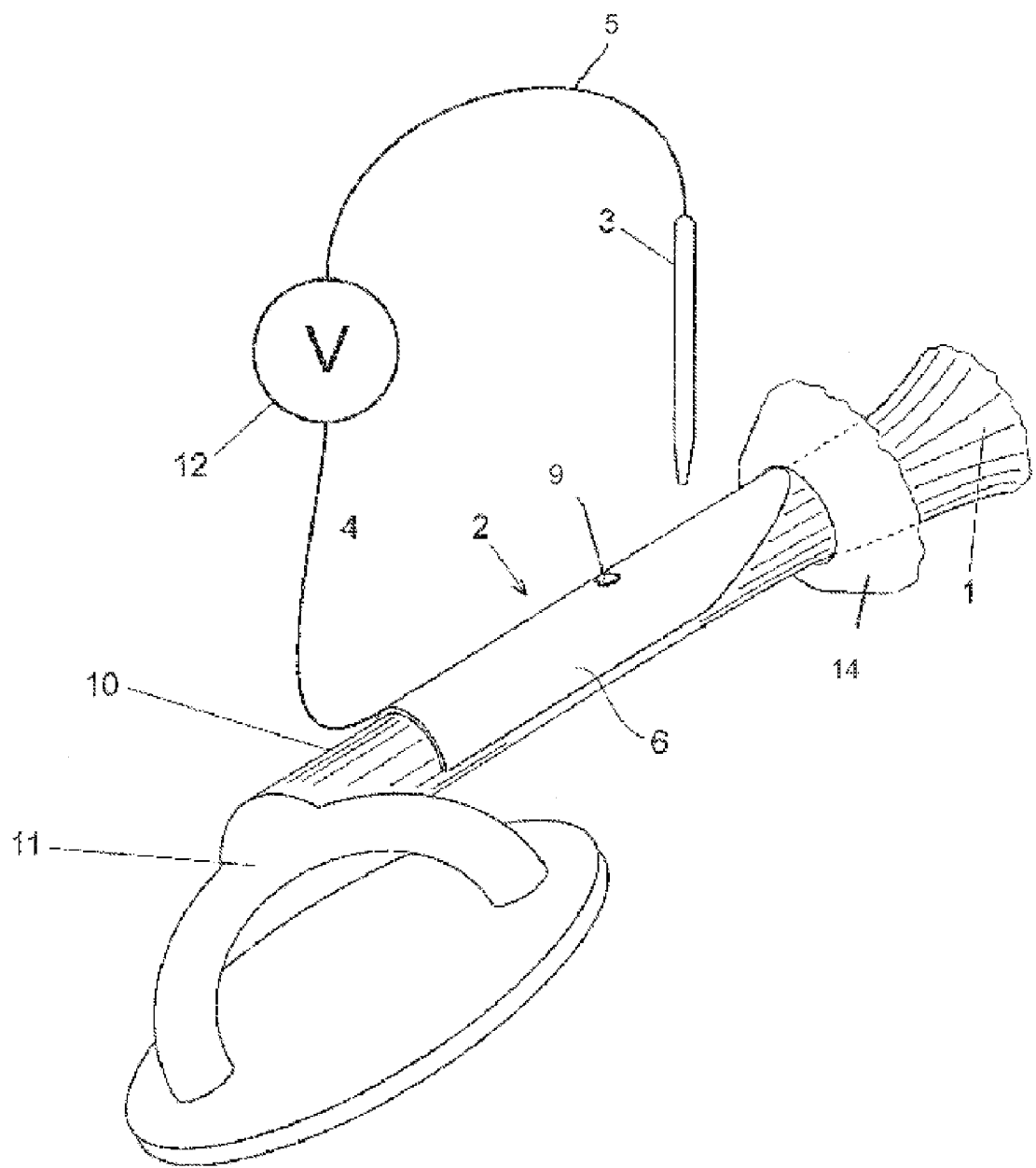
FIG. 6 shows a measuring device according to the invention in a schematic illustration, the first electrode being inserted into the stapedius muscle and the second electrode being inserted into the tendon (before and after the fixation/measurement).
Figure 7:
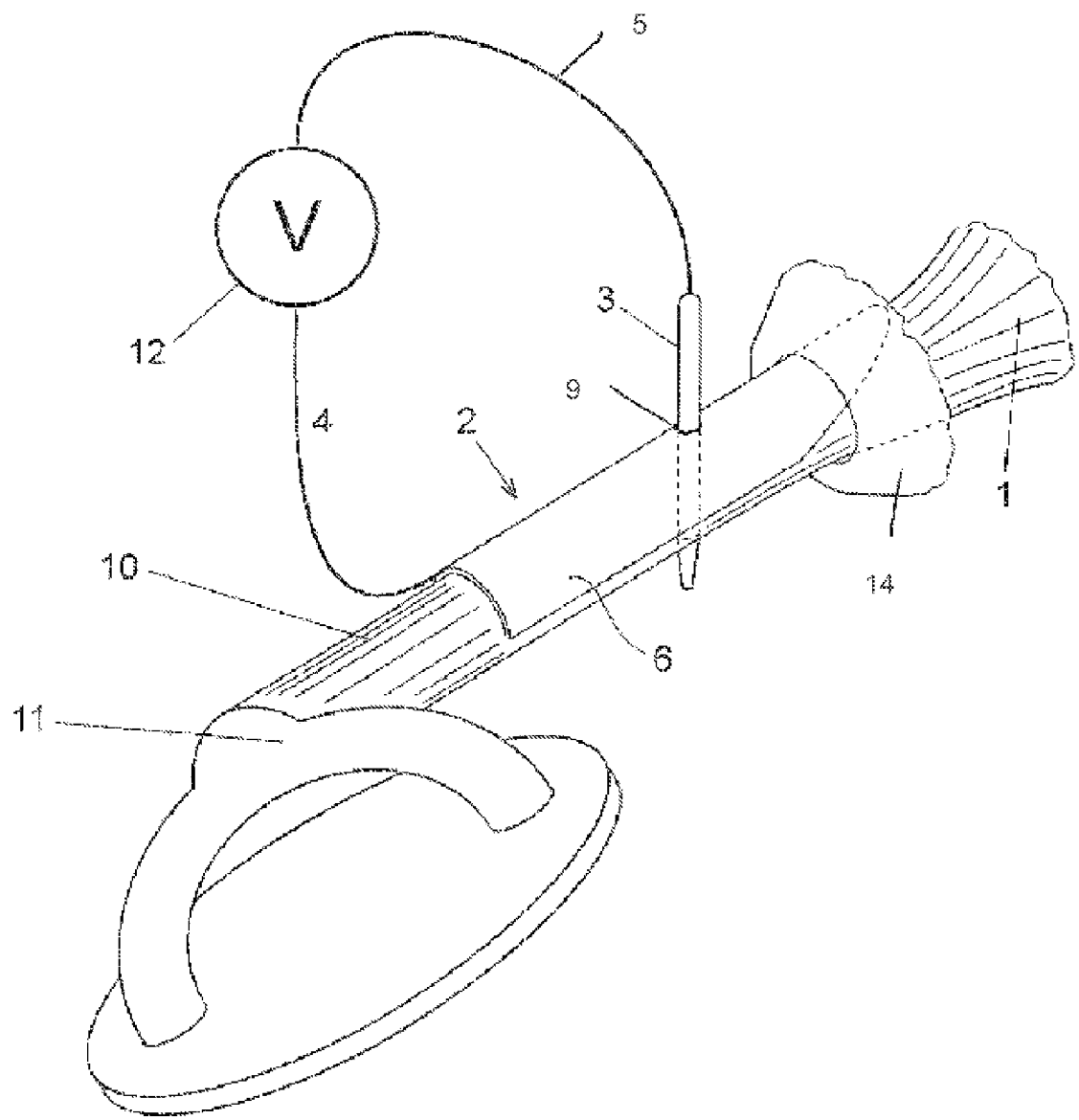
FIG. 7 shows a measuring device according to the invention in a schematic illustration, the first and second electrodes being fixed in the stapedius muscle (during the measurement).

To ensure secure fixation of the main body 6 in electrically active tissue 1, it is provided according to the invention that the main body 6 is fixed using a separate fixation element 3 to be inserted (situated) at an angle in relation to the longitudinal axis of the main body 6. In an especially preferred embodiment variant (FIGS. 2 through 7), the fixation is implemented by a second electrode 3, which is plugged into a through opening 9 of the main body 6 in an especially preferred embodiment variant. A bipolar measuring configuration may thus be provided, the first electrode 2 being connected via the electrical supply line 4 and the second electrode 3 being connected via the electrical supply line 5 to a voltmeter 12 in each case (FIGS. 6 and 7). Because of the existing mobility of the main body 6 along its longitudinal axis inside the muscle tissue 1, secure fixing is achieved using the second electrode 3 by plugging it into the through opening 9 at a finite angle (preferably 60°-90°) to the longitudinal axis of the main body 6, because the plugged-in second electrode 3 blocks the movement of the main body 6 along its longitudinal axis. It is especially preferable to plug the second electrode 3 perpendicularly into the through opening 9 of the main body 6. Alternatively, it is also possible to produce a screw or catch connection between the electrodes 2, 3.

To measure the action potential within the tissue, it is necessary for the electrodes 2, 3 to be electrically insulated from one another in the area in which they are in direct contact. Thus, for example, it is possible that the main body 6 is implemented as electrically conductive and is only electrically insulated in the area 13 of its through opening 9. If only the tip (first end 7) of the main body 6 is located in the muscle tissue 1 (FIGS. 4b and 7), however, it is advantageous to also insulate the remaining main body 6 (except in the area of the first end 7). The electrical supply line 4 (and/or the electrical supply line 5) also must always be electrically insulated in relation to surrounding tissue. Alternatively to the insulation of the main body 6 in the area of the through opening 9, it is possible to insulate the electrode 3 in the area in which it is plugged into the through opening 9. The second electrode 3 and/or its electrical supply 5 and the first electrode 2 and/or its electrical supply 4 (FIG. 4a) must be electrically insulated in an area running to the meter 12 in any case, to be able to implement a punctual measurement of the action potential in the stapedius muscle 1—FIG. 7.

FIGS. 6 and 7 show a possible use of the electrode configuration according to the invention for measuring the action potential of the stapedius muscle 1. For this purpose, it is provided that the main body 6 of the first body 2 is moved using appropriate surgical instruments along the tendon 10, which connects the stapedius muscle 1 to the stirrup 11, into the stapedius muscle 1 (see 6 and 7 and also FIG. 4*a*). The electrode main body 6 may be pushed in the channel (existing between the tendon 10 and the bone 14 surrounding the stapedius muscle 1) (FIG. 7). The second electrode 3 is pushed into the stapedius muscle 1 (alternatively through the through opening 9 and into the tendon 10) separately and (nearly) perpendicularly to the feed direction of the electrode main body 6 according to the invention. Both electrodes 2, 3 are inserted far enough that the first end 7 of the main body 6 at least partially contacts the stapedius muscle 1 and the second electrode 3 engages in the through opening 9 of the electrode main body 6 (FIG. 7) and thus blocks a movement of the electrode body 6 along its longitudinal axis. A reliable determination of the action potential via the connected meter 12 is now possible. However, the first electrode 2 does not have to be completely inserted into the stapedius muscle 1; alternatively, it is also possible to insert the electrode main body 6 only partially into the stapedius muscle 1 (FIGS. 4*a* and 7). In this case, the electrode main body 6 is to be electrically insulated (except in the area of the front end 7). The second electrode 3 may now be inserted into the through opening 9 outside the stapedius muscle 1 (in the area of the tendon 10) and fix the electrode main body 6 for measuring the action potential. The inner area 13 of the through opening 9 is preferably provided with insulation, so that a short-circuit may be avoided between first electrode 2 and second electrode 3 (FIG. 4*b*).

Figure 8:
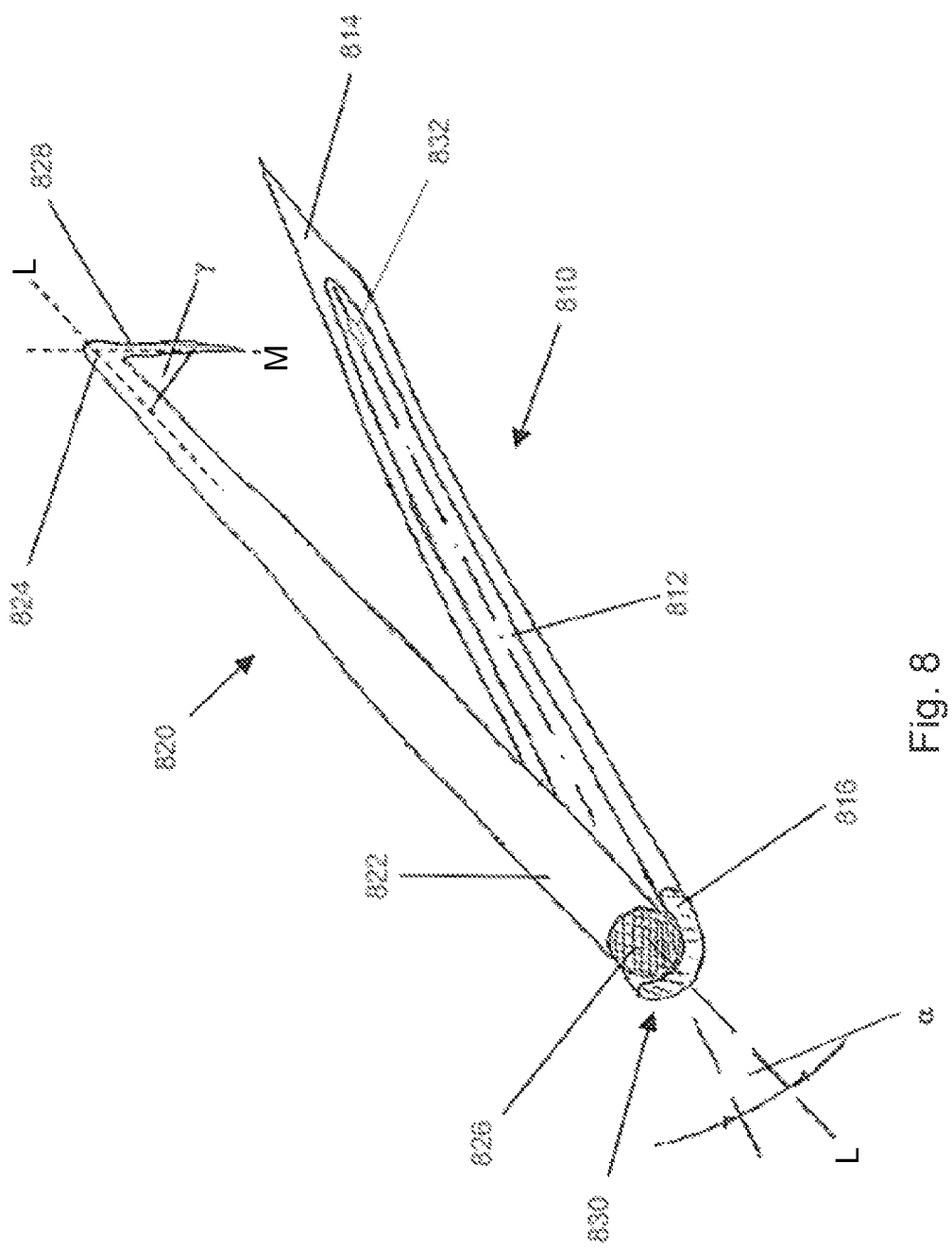
FIG. 8 shows an electrode configuration in the open state according to one specific embodiment of the invention.

FIG. 8 shows an electrode configuration according to another embodiment of the invention for the bipolar measurement of an action current and/or an action potential in target electrically active tissue having a support electrode 810 and a fixation electrode 820. According to the embodiment shown, the support electrode 810 has an elongate support electrode body 812, which, in the embodiment shown, is made of a conductive material formed into an inner cylindrical section surface. Typically, the length of the support electrode body 812 may be about 5 mm, the internal diameter about 1.1 mm, and the sheath thickness about 0.3 mm. The support electrode body 812 has a penetrating end 814 and a base end 816. The penetrating end 814 tapers to a tip. In FIG. 8, the tapering occurs uniformly over 0.5 mm up to a diameter of the tip end of 0.2 mm.

The fixation electrode 820 has an elongate fixation electrode body 822 of about 4 mm in length, and a penetrating end 824 and a base end 826. The diameter of the fixation electrode 820 is typically about 0.3 mm. At the penetrating end 824, the fixation electrode 820 has a penetrating tip 828, whose central axis M forms an angle γ with the longitudinal axis L of the fixation electrode body 822. The angle γ is 90° here, but in other embodiments may be in the range of 80° to 150°. The penetrating tip 828 is implemented here as a wire having a diameter of 0.2 mm and a length of 0.9 mm. The support electrode 810 and fixation electrode 820 may be joined together by a base joint 830 towards the base ends 816 and 826. For example, the base joint 830 may be implemented as a folding hinge. An opening angle α is measured between the longitudinal axes L of the elongate electrode bodies 812 and 822 of the support electrode 810 and the fixation electrode 820 and the opening angle of the base joint may be in the range from 0° to 60°. In the maximally open state, the opening angle α may be around 60°.

The embodiment shown in FIG. 8 thus provides a bipolar sensing electrode arrangement which senses action currents or potentials at two different points in electrically active target tissue, for example, muscle tissue such as stapedius muscle. An action potential can be determined with higher local resolution through a bipolar derivation. The support electrode 810 and the fixation electrode 820 are insulated from one another, especially where they directly touch. At least one of the two electrodes 810 and 820 may have an inner core of conductive material surrounded by an insulating sheath, with the conductive core being exposed around the desired measuring point. These exposed areas should be located away from the region where which the two electrodes 810 and 820 directly contact each other.

The support electrode 810 and the fixation electrode 820 together form a single electrode arrangement where the two electrodes are secured against displacement relative to one another. And in spite of piercing the target tissue, fixation of the electrodes is performed in a way that protects the tissue without trauma. In contrast to the electrodes in the prior art, secure positioning can advantageously be achieved by using both electrodes to pierce the tissue and using shorter piercing lengths. In addition, the two penetrating tips are situated essentially perpendicular to one another so that fixing of the electrode positions is ensured in multiple dimensions. This electrode configuration does not need additional retention mechanisms which are typically traumatic.

The electrode configuration may be specifically implemented as a bipolar measuring configuration where both electrodes are each connected to at least one electrical supply lead and one terminal lead, the supply leads being connected positively and/or non-positively to a voltage and/or current meter. The supply leads and terminal leads may be implemented to be flexible and/or may be made of the same material as the electrodes, but should be electrically insulated in relation to the surrounding tissue. Electrical lines and electrodes can be connected using a soldered, clamp, or welded connection, and the electrical lines can be attached to a voltage and/or current meter using a connection plug as a removable clamp, plug, or screw connection.

The electrodes 810 and 820 should have some intrinsic rigidity near the base ends 816 and 826 to be held and guided during surgical insertion. For example, the electrode bodies 812 and 822 may be implemented from an electrically conductive and rigid material having sufficient bending rigidity, e.g., 200-600 Nmm$^2$, and specifically 450 Nmm$^2$. Examples of specific electrode materials include CrCoMo, Pt, PtIr, Ti, TiAl$_4$V$_6$, or some combination thereof.

In an embodiment such as the one shown in FIG. 8, the base joint 830 may be self-closing, for example, using a biasing spring whose spring force counteracts the opening of the base joint 830. The base joint 830 is thus biased in the closed position and the support electrode 810 and fixation electrode 820 press against one another along their respective electrode bodies 812 and 822. The biasing spring may have a spring constant in the range from 0.1 to 20 N/m, or more specifically in the range from 0.5 to 10 N/m. In some embodiments, there may be one or more structures around the base ends 816 and 826 of the two electrodes for opening the base joint 830, for example, enabling the electrode configuration to be fixed in various opening angles. The base joint 830 may also be implemented so that it can be held, opened, fixed in an open position, closed, and guided using known operating instruments. In the closed state of the base joint 830, the penetrating end 824 of the fixation electrode 820 may be positioned laterally on the electrode body 812 of the support electrode 810. Thus, the electrode body 822 of the fixation electrode 820 may be curved towards the penetrating end 824. This curvature can alternatively also extend over a part or the entire electrode body 822 of the fixation electrode 820. The curvature should be enough so that the penetrating end 824 of the fixation electrode 820 is guided just through the electrode opening in the electrode body 812 of the support electrode 810. In some embodiments there may be even greater curvature so that an intermediate space arises between the electrode body 812 of the support electrode 810 and the penetrating end 824 of the fixation electrode 820.

The electrode body 812 of the support electrode 810 also includes an electrode opening 832 for receiving the penetrating tip 828 of the fixation electrode 820. The shape and dimension of the electrode opening 832 are freely selectable within the scope of the shape and dimension of the penetrating tip 828. The electrode opening 832 may include an electrical insulation layer on its inner surface to provide electrical insulation in the contact region of the electrodes. The insulation layer may be of any appropriate material such as an insulation ceramic, sapphire, or polytetrafluoroethylene (PTFE), and may typically have a thickness of between 10 and 30 µm.

Alternatively or in addition, it is also possible that the penetrating tip 828 of the fixation electrode 820 may have a sheath of electrical insulation such as a silicone or polyurethane elastomer where it contacts the electrode body 812 of the support electrode 810 having a thickness of 0.05 to 0.8 mm, or more specifically, 0.1 to 0.3 mm. For example, an insulation sheath may be formed of plastic, sapphire, or an insulation ceramic. Suitable plastics include without limitation polyethylene, polytetrafluoroethylene, polypropylene, polyurethane elastomers, polyamide, polyimide, polycarbonate, polystyrene, polyvinyl chloride, butyl rubber, a silicone elastomer, an epoxy resin, or a phenol formaldehyde resin. Polytetrafluoroethylene (PTFE) is particularly suitable. Examples of suitable ceramic insulation materials include $A_2O_3$ ceramic, $TiO_2$ ceramic, or glass ceramic.

The support electrode 810 can be completely electrically conductive, as long as the connected electrical supply lead and terminal lead are electrically insulated in relation to the surrounding tissue and the electrode is electrically insulated in relation to the fixation electrode 820. In many embodiments, at least the outer side lateral surface of the support electrode 810 is electrically insulated in relation to the surrounding tissue and/or the fixation electrode 820. The electrode body 822 of the fixation electrode 822 may include a biocompatible insulation sheath which can include the area of the penetrating tip 828 where it has lateral contact with the electrode body 812 of the support electrode 810, leaving at least the end of the penetrating tip 828 which is pierced into the target tissue exposed.

The electrode bodies 812 and 822 of the support electrode 810 and the fixation electrode 820 may assume appropriate shapes so long as they are mutually complementary. For example, in FIG. 8, the electrode body 812 of the support electrode 810 includes a portion shaped as an inner cylindrical section surface which is open along its longitudinal axis which has a circular arc cross-section. The internal diameter of the inner cylindrical section surface may typically be about 0.1 to 1.5 mm, or more specifically, 0.2 to 1.0 mm. The electrode body 822 of the fixation electrode 820 may similarly be implemented as a corresponding hollow or solid cylinder adapted to fit into the inner cylindrical section surface of the electrode body 812 of the support electrode 810, for example, having a diameter in the range from 0.1 to 1.5 mm, or more specifically, 0.2 to 1.0 mm. If the internal diameter of the inner cylindrical section surface of the support electrode 810 is greater than or equal to the outer diameter of the fixation electrode 820, then fabrication of the base joint 830 is simplified. The length of the electrode body 822 of the fixation electrode 820 may be in the range from 1 to 10 mm, e.g., 2 to 5 mm long, with the length of the electrode body 812 of the support electrode 810 being typically 101% to 120% that of the fixation electrode 820, e.g., 105% to 110%. Such typical dimensions are particularly suitable for guiding the electrode configuration during surgical insertion while protecting the surrounding tissue such as the stapedius muscle and the associated tendon and bone.

Typically the penetrating end 814 of the support electrode 810 uniformly tapers to a tip in a portion of the support electrode 810 beyond the electrode body 822 of the fixation electrode 820. The diameter is preferably 0.1 to 0.5 mm, more preferably 0.05 to 0.2 mm, at the end of the tip, i.e., at the point having the smallest diameter. In a further preferred embodiment, the electrode body of the support electrode preferably has a bevel in the area of the tip of its first end, which has an angle between 30° and 60° to the longitudinal axis of the electrode body. Insertion of the support electrode which protects tissue is thus made possible. The penetrating tip 828 of the fixation electrode 820 may have a length of 0.1 to 2 mm, e.g., 0.5 to 1 mm. The end of the penetrating tip 828 which enters into the target tissue may have a diameter of 0.1 to 0.5 mm, e.g., 0.1 to 0.2 mm; for example, this may be a wire having a uniform diameter or a cone having a circular or polygonal footprint. The lateral surfaces of the cone may taper uniformly, or have a concave or convex bulge. The penetrating tip 828 may be implemented as a drop-shaped disc, observed from the viewing direction in the direction of the front face of the penetrating end 824. The transition to the electrode body 822 of the fixation electrode 820 may occur in the form of a concave or convex bulge. Shape changes to optimize the piercing into the tissue or the manufacturing of the electrode are also included.

Figure 9:
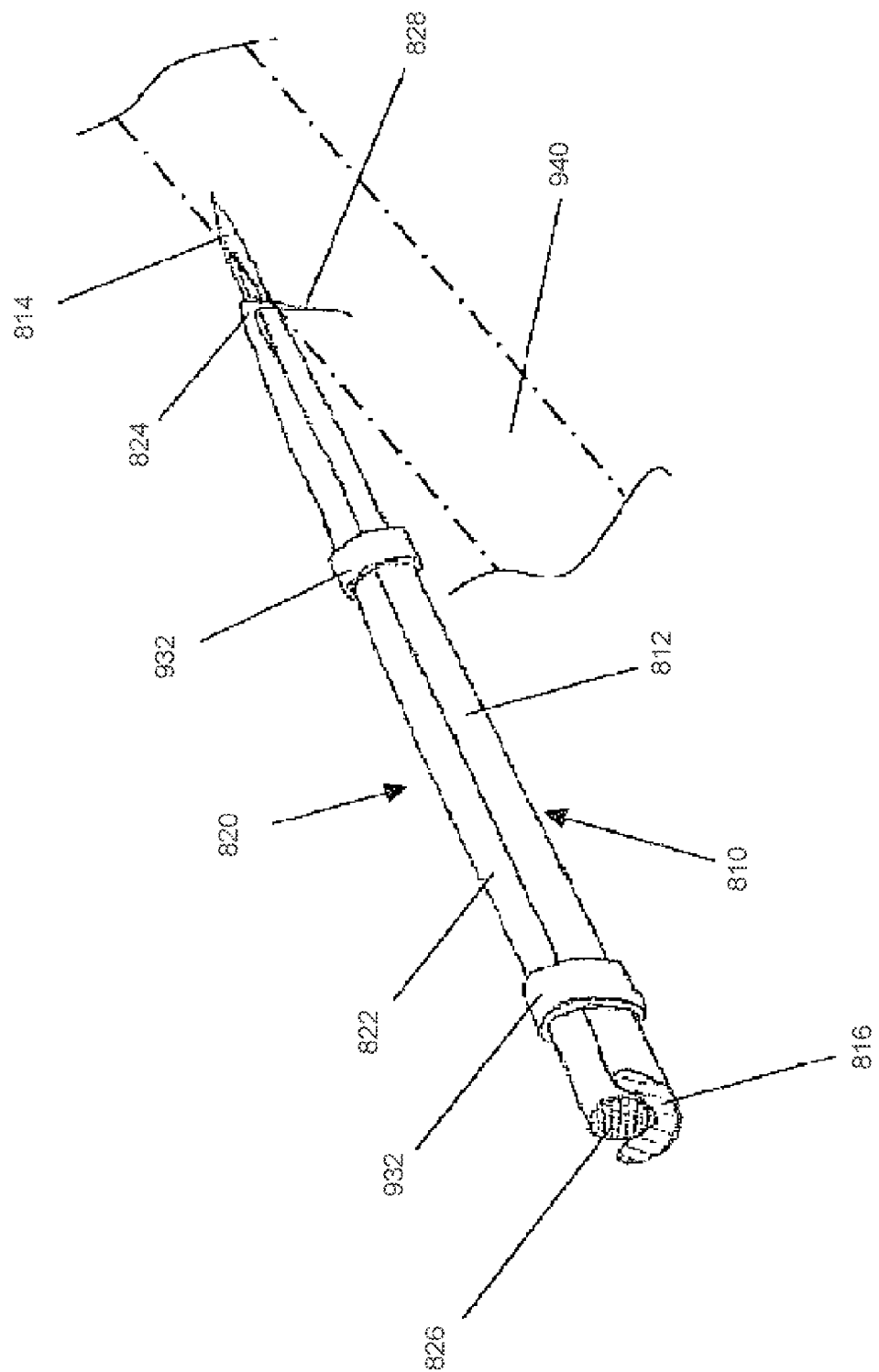
FIG. 9 shows an electrode configuration in the closed state according to one specific embodiment of the invention.

FIG. 9 shows another embodiment of electrode configuration having a closed connection joint and applied in the electrically active target tissue 940 such as stapedius muscle tissue. The penetrating tip 828 of the fixation electrode 820 is guided laterally through an electrode opening 832 toward the penetrating end of the support electrode 810. For this purpose, the fixation electrode 820 may be slightly curved in the area of the penetrating end 824. The penetrating end 814 of the support electrode 810 is tapered to a tip and inserted into the electrically active tissue 940. The penetrating tip 828 of the fixation electrode 820 also is inserted into the electrically active tissue 940. The two tips 814 and 828 secure one another mutually against slipping out of position from the target tissue. Secure fixing of the electrode configuration in the tissue is thus made possible. In addition, the two electrodes 810 and 820 are fixed in relation to one another using clamping rings 932.

To measure the action potential within the target tissue 940, the electrodes 810 and 820 should be electrically insulated from one another where they are in direct contact. Thus, for example, it is possible that the support electrode body 812 is implemented as electrically conductive and the fixation electrode body 822 as electrically insulated. The insulation of the fixation electrode body 822 may be a layer of insulating material such as n insulation ceramic, sapphire, or polytetrafluoroethylene (PTFE), and has a thickness between 10 and 30 μm. Alternatively, it is also possible that the tip of the fixation electrode 820 has electrical insulation in the area in which it contacts the electrode body of the support electrode 810. This electrical insulation may be a silicone or polyurethane elastomer. The layer of electrical insulation may extend into the penetrating tip 828 to the electrode opening 832 of the support electrode 810. Because only the tip of the penetrating end 814 of the support electrode body 812 is located in the electrically active tissue 940, it may be advantageous to also insulate the remaining support electrode body 812 on the outer side of the lateral surface, except in the area of the penetrating end 814. The base ends 816 and 826 should remain electrically accessible, in order to be able to pick up the measured potentials using electrical leads, for example.

Figure 10:
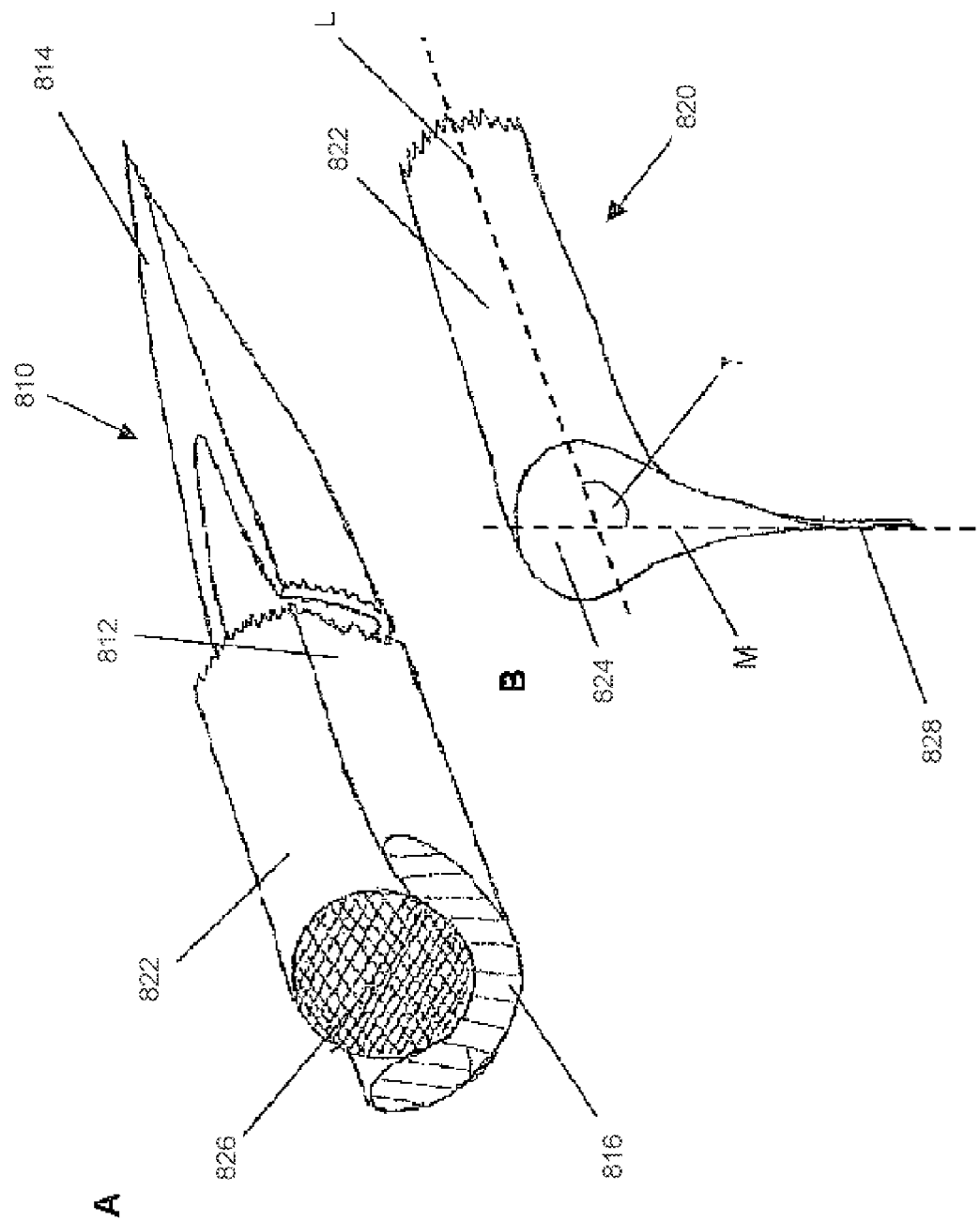
FIG. 10 shows various structural details of the ends of the electrodes in FIGS. 8 and 9.

FIG. 10 A-B shows structural details of the penetrating ends 814 and 824 and the base ends 816 and 826 of the support electrode 810 and the fixation electrode 820. The electrode body 822 of the fixation electrode 820, implemented as a cylinder here, and lies in the inner cylindrical section surface of the electrode body 812 of the support electrode 810. The base ends 816 and 826 actively press against each other.

FIG. 10A shows a detailed view of the penetrating end 814 of the support electrode 810, which is shaped into a tip. The lateral tapering occurs continuously over a length of 0.5 mm. The internal diameter of the inner cylindrical section surface is reduced until the two side lateral surfaces abut one another, then the tip is provided as a half section cylinder. The tapering of the tip occurs from the bottom side, i.e., the side having the convex external curvature, so that the lateral surface is not penetrated. A bevel occurs at an angle between 30° and 60° to the longitudinal axis of the main body. Insertion of the support electrode 810 in a way which protects the target tissue is thus made possible.

FIG. 10B shows the penetrating end 824 of the fixation electrode 820 in detail. The front side of the penetrating end 824 is lengthened in a drop shape beyond the diameter of the electrode body 822 into a penetrating tip 828. The minimal diameter of the penetrating tip 828 is at the tip end and is 0.05 mm. A tip axis M leads through the center point of the front side of the electrode body 822 and the drop tip, i.e., the narrowest point of the penetrating tip 828. The angle γ between the tip axis M and the longitudinal axis L of the electrode body 822 is 90°. In some embodiments, the tip axis M may be rotatable about the longitudinal axis L. This feature is useful for embodiments where there is electrode opening 832, but instead where the penetrating end 824 of the fixation electrode 820 penetrates tissue to the left or right of the penetrating end 814 of the support electrode 810.

Although various exemplary embodiments of the invention have been disclosed, it should be apparent to those skilled in the art that various changes and modifications can be made which will achieve some of the advantages of the invention without departing from the true scope of the invention.

What is claimed is:

1. An electrode arrangement for sensing electrical activity in target tissue, the arrangement comprising:
    an elongated support electrode formed with an inner cylindrical section surface and having a base end and a support electrode penetrating end configured for insertion into the target tissue;
    an elongated fixation electrode formed to fit into the inner cylindrical section surface of the support electrode and having a base end adjacent and mechanically connected to the base end of the support electrode and a fixation electrode penetrating end forming a right angle to the fixation electrode; and
    an electrode opening towards the support electrode penetrating end through which fits the fixation electrode penetrating end;
    wherein the electrodes are joined together in parallel so that the fixation electrode penetrating end penetrates a fixed distance through the electrode opening into the target tissue so that at least one of the electrodes senses electrical activity in the target tissue.

2. An electrode arrangement according to claim 1, further comprising:
    an electrical insulation layer in the electrode opening for electrically isolating the support electrode from the fixation electrode.

3. An electrode arrangement according to claim 2, wherein the electrical insulation layer is ceramic, sapphire, $A_2O_3$, $TiO_2$, or glass.

4. An electrode arrangement according to claim 2, wherein the electrical insulation layer has a thickness between 10 μm and 30 μm.

5. An electrode arrangement according to claim 1, further comprising:
    an electrical output connection at one of the base ends to provide an electrical output signal representing the sensed electrical activity.

6. An electrode arrangement according to claim 1, further comprising:
    a fixation connector surrounding and mechanically connecting the electrodes.

7. An electrode arrangement according to claim 6, wherein the fixation connector is movable.

8. An electrode arrangement according to claim 1, wherein the electrode arrangement forms a monopolar sensing arrangement.

9. An electrode arrangement according to claim 1, wherein the electrode arrangement forms a bipolar sensing arrangement.

10. An electrode arrangement according to claim 1, further comprising:
    an electrical insulation layer covering at least a portion of at least one of the electrodes.

11. An electrode arrangement according to claim 10, wherein the electrical insulation layer is silicone or polyurethane elastomer.

* * * * *